(12) United States Patent
Klisch et al.

(10) Patent No.: US 9,017,308 B2
(45) Date of Patent: Apr. 28, 2015

(54) INSERT MOLDED HUB AND STRAIN RELIEF

(75) Inventors: Leo Klisch, Maple Grove, MN (US); August Powell, Zimmerman, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 822 days.

(21) Appl. No.: 10/152,426

(22) Filed: May 21, 2002

(65) Prior Publication Data
US 2003/0220628 A1 Nov. 27, 2003

(51) Int. Cl.
*A61M 25/00* (2006.01)
*A61M 31/00* (2006.01)

(52) U.S. Cl.
CPC ... *A61M 25/0097* (2013.01); *A61M 2025/0098* (2013.01)

(58) Field of Classification Search
USPC .............. 285/148.23; 606/192, 194; 604/506, 604/508–535, 164.1, 537, 284, 256, 98.02, 604/110, 500, 264–268, 194, 93.01, 96.01, 604/98.01
See application file for complete search history.

(56) References Cited

U.S. PATENT DOCUMENTS

| | | | |
|---|---|---|---|
| 2,185,741 A | 1/1940 | Sorg et al. | |
| RE25,788 E | 6/1965 | Sheridan | |
| 3,318,335 A | 5/1967 | Heller | |
| 3,348,544 A | 10/1967 | Braun | |
| 3,470,869 A | 10/1969 | Fenton et al. | |
| 3,633,758 A | 1/1972 | Morse | |
| 3,720,210 A | 3/1973 | Diettrich | |
| 3,725,522 A | 4/1973 | Sheridan et al. | |
| 3,752,510 A | 8/1973 | Windischman et al. | |
| 3,861,972 A | 1/1975 | Glover et al. | |
| 3,865,666 A | 2/1975 | Shoney | |
| 3,873,391 A | 3/1975 | Plauka et al. | |
| 3,914,002 A | 10/1975 | Berliner et al. | |
| 3,950,052 A | 4/1976 | Walter et al. | |
| 3,959,429 A | 5/1976 | Benning | |
| 3,985,601 A | 10/1976 | Panagrossi | |
| 3,989,571 A | 11/1976 | Harautuneian | |
| 4,085,185 A | 4/1978 | Adair | |
| 4,093,484 A | 6/1978 | Harrison et al. | |
| 4,154,244 A | 5/1979 | Becker et al. | |
| 4,171,943 A | 10/1979 | Tschanz et al. | |
| 4,187,848 A * | 2/1980 | Taylor ........................... | 604/243 |
| 4,191,185 A | 3/1980 | Lemieux | |

(Continued)

FOREIGN PATENT DOCUMENTS

EP 0 437 291 B1 7/1991
EP 0 782 868 A1 7/1997

(Continued)

OTHER PUBLICATIONS

Mauch, Bifucated Catheter Assembly, US Patent Pub No. US 2001/0012927, Aug. 9, 2001.*

(Continued)

*Primary Examiner* — Andrew Gilbert
(74) *Attorney, Agent, or Firm* — Seager, Tufte & Wickhem, LLC

(57) ABSTRACT

A hub assembly and methods of attaching the same to a catheter shaft. The hub assembly includes a strain relief coupled to a hub. The strain relief may be mechanically coupled to the hub. The hub assembly may be manufactured in a non-clean room environment, and subsequently connected to the catheter shaft in a clean room.

6 Claims, 1 Drawing Sheet

(56) References Cited

U.S. PATENT DOCUMENTS

| | | | |
|---|---|---|---|
| 4,198,983 A | 4/1980 | Becker et al. | |
| 4,207,900 A | 6/1980 | Patel et al. | |
| 4,210,478 A | 7/1980 | Shoney | |
| 4,284,459 A | 8/1981 | Patel et al. | |
| 4,314,555 A * | 2/1982 | Sagae | 604/168.01 |
| 4,326,519 A | 4/1982 | D'Alo et al. | |
| 4,328,056 A | 5/1982 | Snooks | |
| 4,354,495 A | 10/1982 | Bodicky | |
| 4,489,961 A | 12/1984 | Laidig | |
| 4,509,877 A | 4/1985 | Sobin et al. | |
| 4,511,163 A | 4/1985 | Harris et al. | |
| 4,531,943 A | 7/1985 | Van Tassel et al. | |
| 4,557,781 A | 12/1985 | Hoppie | |
| 4,592,749 A | 6/1986 | Ebling et al. | |
| 4,596,563 A | 6/1986 | Pande | |
| 4,602,808 A | 7/1986 | Herron et al. | |
| 4,607,746 A | 8/1986 | Stinnette | |
| 4,655,762 A | 4/1987 | Rogers | |
| 4,737,219 A | 4/1988 | Taller et al. | |
| 4,753,765 A | 6/1988 | Pande | |
| 4,778,550 A | 10/1988 | Barton et al. | |
| 4,806,182 A | 2/1989 | Rydell et al. | |
| 4,826,480 A | 5/1989 | Diaz et al. | |
| 4,838,269 A | 6/1989 | Robinson et al. | |
| 4,842,590 A | 6/1989 | Tanabe et al. | |
| 4,863,441 A | 9/1989 | Lindsay et al. | |
| 4,863,442 A | 9/1989 | DeMello et al. | |
| 4,874,373 A | 10/1989 | Luther et al. | |
| 4,875,481 A * | 10/1989 | Higgins | 606/194 |
| 4,886,506 A | 12/1989 | Lovgren et al. | |
| 4,950,257 A | 8/1990 | Hibbs et al. | |
| 4,959,067 A | 9/1990 | Muller | |
| 4,960,412 A | 10/1990 | Fink | |
| 5,031,775 A | 7/1991 | Kane | |
| 5,035,686 A | 7/1991 | Crittenden et al. | |
| 5,041,095 A | 8/1991 | Littrell | |
| 5,085,645 A | 2/1992 | Purdy et al. | |
| 5,125,903 A | 6/1992 | McLaughlin et al. | |
| 5,125,913 A | 6/1992 | Quackenbush | |
| 5,129,887 A | 7/1992 | Euteneuer et al. | |
| 5,139,032 A | 8/1992 | Jahrmarkt et al. | |
| 5,143,409 A | 9/1992 | Lalikos | |
| 5,160,559 A | 11/1992 | Scovil et al. | |
| 5,167,647 A | 12/1992 | Wijkamp et al. | |
| 5,181,750 A | 1/1993 | Reum | |
| 5,190,529 A | 3/1993 | McCrory et al. | |
| 5,201,723 A | 4/1993 | Quinn | |
| 5,217,555 A | 6/1993 | Franklin, III et al. | |
| 5,221,270 A | 6/1993 | Parker | |
| 5,226,898 A | 7/1993 | Gross | |
| 5,240,537 A | 8/1993 | Bodicky | |
| 5,248,305 A | 9/1993 | Zdrahala | |
| 5,254,107 A | 10/1993 | Soltesz | |
| 5,279,596 A | 1/1994 | Castaneda et al. | |
| 5,300,032 A | 4/1994 | Hibbs et al. | |
| 5,312,356 A | 5/1994 | Engelson et al. | |
| 5,318,032 A | 6/1994 | Lonsbury et al. | |
| 5,330,444 A | 7/1994 | Webler et al. | |
| 5,330,449 A | 7/1994 | Prichard et al. | |
| 5,358,493 A * | 10/1994 | Schweich et al. | 604/264 |
| 5,366,444 A | 11/1994 | Martin | |
| 5,376,077 A | 12/1994 | Gromringer | |
| 5,380,301 A | 1/1995 | Prichard et al. | |
| 5,395,332 A | 3/1995 | Ressemann et al. | |
| 5,403,292 A | 4/1995 | Ju | |
| 5,466,230 A | 11/1995 | Davila | |
| 5,496,294 A * | 3/1996 | Hergenrother et al. | 604/524 |
| 5,507,300 A | 4/1996 | Mukai et al. | |
| 5,507,728 A | 4/1996 | Erskine | |
| 5,533,988 A | 7/1996 | Dickerson et al. | |
| 5,545,151 A | 8/1996 | O'Connor et al. | |
| 5,558,635 A | 9/1996 | Cannon | |
| 5,558,652 A | 9/1996 | Henke | |
| 5,569,218 A | 10/1996 | Berg | |
| 5,599,325 A | 2/1997 | Ju et al. | |
| 5,607,055 A | 3/1997 | Bettinger | |
| 5,695,467 A | 12/1997 | Miyata et al. | |
| 5,762,637 A | 6/1998 | Berg et al. | |
| 5,803,510 A | 9/1998 | Dorsey, III | |
| 5,830,401 A | 11/1998 | Prichard et al. | |
| 5,897,537 A | 4/1999 | Berg et al. | |
| 5,897,584 A | 4/1999 | Herman | |
| 5,964,737 A * | 10/1999 | Caizza | 604/239 |
| 5,993,399 A | 11/1999 | Pruitt et al. | |
| 5,997,562 A * | 12/1999 | Zadno-Azizi et al. | 606/194 |
| 6,042,578 A | 3/2000 | Dinh et al. | |
| 6,047,825 A | 4/2000 | Samuels | |
| 6,053,313 A | 4/2000 | Farrell et al. | |
| 6,068,121 A | 5/2000 | McGlinch | |
| 6,068,622 A * | 5/2000 | Sater et al. | 604/524 |
| 6,228,073 B1 | 5/2001 | Noone et al. | |
| 6,273,404 B1 | 8/2001 | Holman et al. | |
| 6,332,874 B1 | 12/2001 | Eliasen et al. | |
| 6,440,119 B1 * | 8/2002 | Nakada et al. | 604/506 |
| 6,500,157 B2 * | 12/2002 | Luther | 604/264 |
| 6,520,951 B1 * | 2/2003 | Carrillo et al. | 604/516 |
| 6,575,959 B1 * | 6/2003 | Sarge et al. | 604/533 |
| 6,620,149 B1 * | 9/2003 | Lenz et al. | 604/524 |

FOREIGN PATENT DOCUMENTS

| | | |
|---|---|---|
| EP | 0 937 480 A1 | 8/1999 |
| FR | 2092970 | 1/1972 |
| GB | 2 187 670 A | 9/1987 |

OTHER PUBLICATIONS

U.S. Appl. No. 09/472,265, filed Dec. 27, 1995, Sarge et al.

* cited by examiner

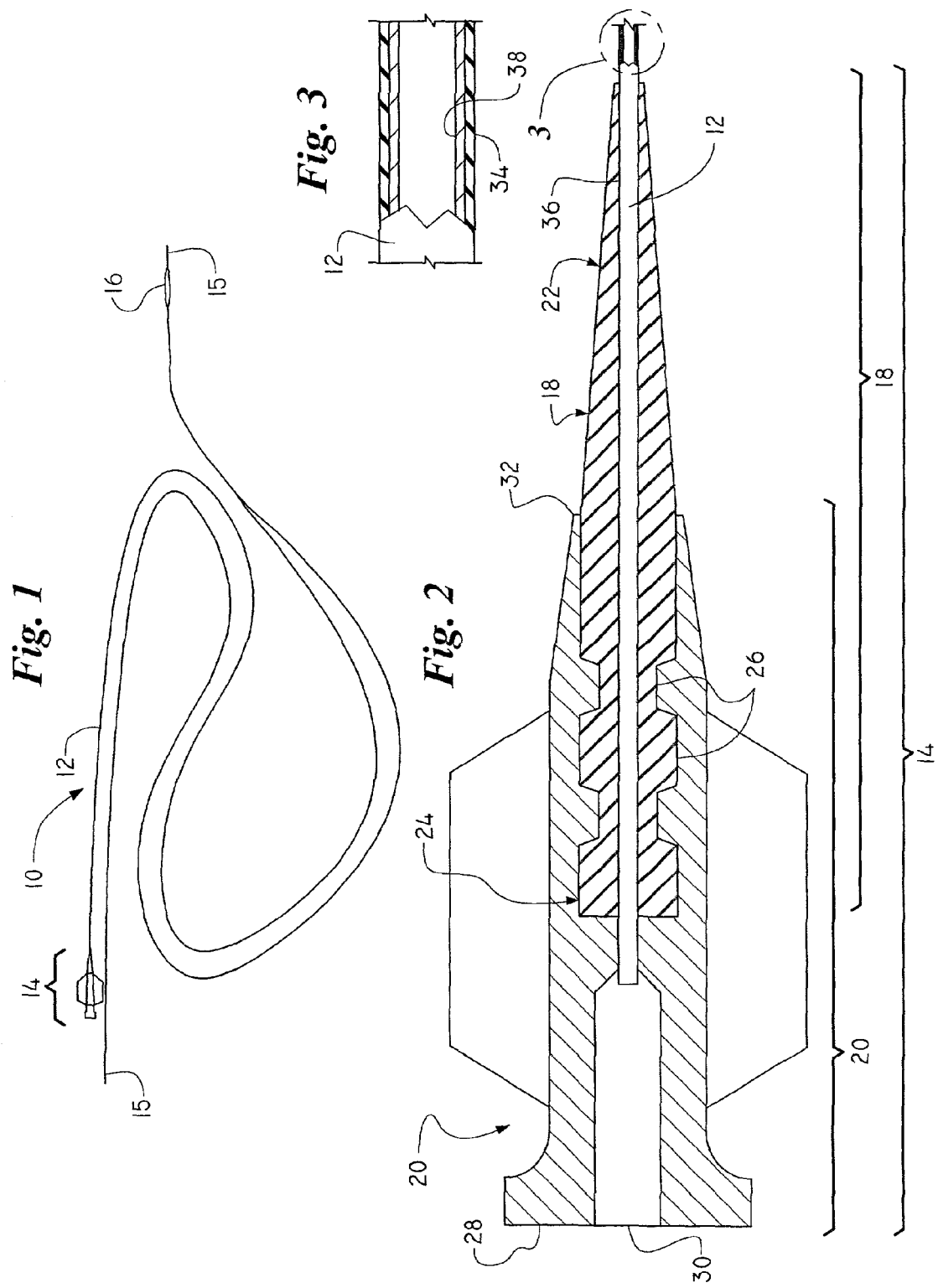

US 9,017,308 B2

INSERT MOLDED HUB AND STRAIN RELIEF

FIELD OF THE INVENTION

The present invention pertains to catheters for use in medical procedures. More particularly, the present invention pertains to an improved catheter hub and strain relief assembly for attaching to a catheter shaft.

BACKGROUND OF THE INVENTION

The use of intravascular catheters has become an effective method for treating many types of vascular disease. In general, an intravascular catheter is inserted into the vascular system of the patient and navigated through the vasculature to a desired target site. Using this method, virtually any target site in the patient's vascular system may be accessed, including the coronary, cerebral, and peripheral vasculature. Examples of therapeutic purposes for intravascular catheters include percutaneous transluminal angioplasty (PTA) and percutaneous transluminal coronary angioplasty (PTCA).

When in use, intravascular catheters enter a patient's vasculature at a convenient location and then are urged to a target region. Once the distal portion of the catheter has entered the patient's vascular system the physician may urge the distal tip forward by applying longitudinal forces to the proximal portion of the catheter. For the catheter to effectively communicate these longitudinal forces, it is desirable that the catheter have a high level of pushability and kink resistance particularly near the proximal end.

Frequently the path taken by a catheter through the vascular system is tortuous, requiring the catheter to change direction frequently. In some cases, it may even be necessary for the catheter to double back on itself. In order for the catheter to conform to a patient's tortuous vascular system, it is desirable that intravascular catheters be very flexible, particularly near the distal end.

Further, while advancing the catheter through the tortuous path of the patient's vasculature, physicians often apply torsional forces to the proximal portion of the catheter to aid in steering the catheter. Torsional forces applied on the proximal end must translate to the distal end to aid in steering. It is therefore desirable that the proximal portion of an intravascular catheter have a relatively high level of torqueability to facilitate steering.

The need for this combination of performance features is often addressed by manufacturing a catheter that has two or more discrete tubular members having different performance characteristics. For example, a relatively flexible distal section may be connected to a relatively rigid proximal section. When a catheter is formed from two or more discrete tubular members, it is often necessary to form a bond between the distal end of one tubular member and the proximal end of another tubular member.

To facilitate manipulation of the proximal end of the catheter, and to interface with ancillary devices (e.g., inflation device, guide wire, etc.), catheters commonly include a proximal hub or manifold. The hub often includes a port or connector for connecting the catheter to, for example, an inflation device or means for conveying a fluid media into the catheter. The hub may also include a port for insertion of a guide wire into the catheter. In some known catheters, hubs are adhesively bonded to the catheter shaft together with a tubular strain relief.

BRIEF SUMMARY OF THE INVENTION

The present invention relates to the field of catheterization of lumens within the human body, particularly lumens in the cardiac, peripheral, and neurological vasculature. The invention has application to the manufacture and construction of a wide variety of catheters, including, without limitation, guide, diagnostic, and drug delivery catheters, as well as balloon catheters. The present invention includes a novel hub assembly that is adapted and configured to be attached to a catheter shaft.

The hub assembly may include a strain relief and a hub. The strain relief includes a proximal portion and a distal portion. The distal portion may be configured to provide structural support to the catheter shaft. The hub may be molded to at least the proximal portion of the strain relief. Moreover, the proximal portion of the strain relief may be mechanically interlocked with the hub, for example by one or more grooves on the proximal portion of the strain relief.

BRIEF DESCRIPTION OF THE SEVERAL VIEWS OF THE DRAWINGS

FIG. 1 is a plan overview of an intravascular catheter including a novel hub assembly;

FIG. 2 is an enlarged cross-sectional view the hub assembly coupled to a catheter shaft; and FIG. 3 is an enlarged sectional view indicated by section 3 in FIG. 2.

DETAILED DESCRIPTION OF THE INVENTION

The following description should be read with reference to the drawings wherein like reference numerals indicate like elements throughout the several views. The detailed description and drawings illustrate example embodiments of the claimed invention, and are not intended to be limiting.

FIG. 1 is a plan overview of a catheter 10, shown by way of example as an intravascular balloon catheter 10 disposed on an intravascular guide wire 15. Catheter 10 includes an elongate shaft 12 having a proximal portion and a distal portion. One or more lumens (not shown) may be disposed within shaft 12. The lumens may be used for any one of many functions known in such catheter devices. A hub assembly 14 is connected to the proximal portion of the shaft 12 and a balloon 16 is connected to the distal portion of the shaft 12.

Hub assembly 14 is designed, for example, to make it possible to manufacture different portions of catheter 10 in separate locations. According to this embodiment, hub assembly 14 may be manufactured in a molding shop or other suitable location and then be moved to a clean room where catheter 10 is being manufactured. Inside the clean room, hub assembly 14 may be attached to shaft 12. Because of this feature, an assembler no longer needs to remove the entire catheter 10 (including shaft 12 that may be 150 cm or more in length) into a "non-clean" environment for attachment to the hub by insert-molding. Moreover, by eliminating the need to move the shaft 12 from room to room, the probability of damaging catheter 10 during manufacturing is reduced. These advantages of the present invention and others will be discussed in more detail below.

Hub assembly 14 may be used with a number of different catheters including guide, diagnostic, and therapeutic catheters. Catheter 10 illustrated in FIG. 1 comprises an angioplasty balloon catheter by way of example, not limitation. It can be appreciated that the hub assembly 14 could also be used in conjunction with stent delivery catheters, atherectomy devices, embolic protection devices, non-intravascular catheters, etc.

FIG. 2 is an enlarged, cross sectional view of hub assembly 14. From this illustration it can be seen that assembly 14 includes a strain relief 18 and a hub 20. Strain relief 18 may be polymeric and may include a tapered distal region 22 configured to provide structural support for shaft 12. By providing structural support, strain relief 18 may help to avoid kinking shaft 12 at the junction of shaft 12 and the hub 20.

Strain relief 18 also includes a proximal region 24 having a mechanically interlockable geometry, such as one or more retaining grooves 26. The interlocking geometry on the outside of the strain relief 18 mates with a corresponding geometry on the inside of the hub 20. Retaining grooves 26 allow strain relief 18 to be mechanically locked with hub 20.

According to this embodiment, strain relief 18 and hub 20 would not need to be thermally or adhesively bonded together. In fact, the thermal properties of strain relief 18 and hub 20 would not need to be compatible and/or strain relief 18 and hub 20 may be comprised of different materials. This feature would allow, for example, strain relief 18 and/or hub 20 to be comprised of generally transparent materials that would remain transparent throughout the construction of catheter 10 (i.e., would not become opaque due to thermal bonding or adhesive bonding). In addition, this feature would allow strain relief 18 to be comprised of a generally flexible material relative to the material of the hub 20. Alternatively, strain relief 18 and hub 20 may be comprised of thermal bond compatible materials. This would allow for bonding to occur during injection molding. These features would allow for a plethora of different materials and configurations for constructing assembly 14.

To construct assembly 14, at least a proximal portion of strain relief 18 may be inserted into a mold so that hub 20 may be molded thereto. The molding procedure is essentially the same as known insert molding techniques. Generally, after placing strain relief 18 into the mold, molten polymer is infused, injected, or otherwise disposed within the mold and then allowed to cool. Once cooled, the polymer within the mold solidifies and forms hub 20. According to this embodiment, at least a portion of hub 20 may be molded over grooves 26. Grooves 26 would then mechanically lock hub 20 and strain relief 18.

Alternatively, hub 20 may be thermally bonded (e.g., laser bonded) to strain relief 18. According to this embodiment, strain relief 18 and hub 20 could be joined in a manufacturing step that is separate from formation of both components. Generally, thermal bonding includes placing strain relief 18 and hub 20 adjacent each other in a configuration appropriate for forming assembly 14. Once adjacent, strain relief 18 and hub 20 may be heated so as to at least partially melt and form a bond therebetween. When thermally bonding hub 20 and strain relief 18, it may be desirable for hub 20 and strain relief 18 to have similar melting points.

Hub 20 includes a proximal end 28 with a proximal port 30, and a distal end 32. Proximal port 30 may be used to connect catheter 10 to a number of different ancillary devices. For example, port 30 may be used to connect catheter 10 to an inflation device or means for delivering fluid media. It can be appreciated that hub 20 could equivalently be described as a manifold without departing from the spirit of the invention. For example, hub 20 may include additional lumens or ports and be referred to as a manifold.

Shaft 12 may be constructed of a polymeric, metallic, or composite tube. For example, as seen in FIG. 3, shaft 12 may include an inner tube 38 and an outer polymeric member 34 disposed at a proximal end 36 thereof and extend at least partially along the length of shaft 12. Polymeric member 34 may comprise, for example, an outer sheath, outer coating, tube, or other suitable structure. Polymeric member 34 may be used to help attach strain relief 18 to shaft 12 by providing a substrate for molding or otherwise joining strain relief 18.

Strain relief 18 may be attached to shaft 12 (and/or polymeric member 34) by a number of techniques. For example, distal region 22 of strain relief 18 may be thermal (e.g., laser) bonded to polymeric member 34. This technique may be particularly useful because the necessary equipment and expertise would be available in the "clean room" to perform the bonding because similar methods may be used to join balloons to catheter shafts (including balloon 16 to shaft 12). Alternatively, distal region 22 may be coupled to shaft 12 by adhesive bonding or other suitable techniques. Strain relief 18 has sufficient structural integrity to provide a robust connection to shaft 12 without the need for a separate connection between shaft 12 and hub 20.

Strain relief 18 may also serve as a thermal insulator to protect shaft 12 from heat during, for example, thermal bonding. More particularly, strain relief 18 may have a suitable thickness to protect shaft 12 from heat during thermal bonding steps. This feature is important because embodiments of shaft 12 often have a relatively thin wall, which could be deformed or otherwise damaged by heat. Another way of insulating shaft 12 from heat is disclosed in U.S. patent application Ser. No. 09/472,265 to Sarge et al., the entire disclosure of which is incorporated by reference, wherein a protective sleeve is disposed over shaft 12. It can be appreciated that polymeric member 34 can be adapted to perform the same function.

Both distal portion 22 and proximal portion 24 of strain relief 18 may include thickened areas to protect shaft 12 from heat. For example, proximal portion 24 may have a first thickness at grooves 26 and a second thickness between grooves 26. The second thickness would be sufficient to insulate shaft 12 from heat above the melting temperature or glass transition temperature of either hub 20 or strain relief 18. For example, the first thickness may be greater than about 0.14 inches and the second thickness may be greater than about 0.10 inches.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A method of attaching a hub to a catheter shaft, comprising:
   providing a strain relief;
   inserting at least a portion of the strain relief into a mold;
   injecting a polymeric material into the mold to form a hub having a distal end such that at least a portion of the strain relief extends into the hub and such that no portion of the strain relief proximal of the distal end of the hub is outside the hub;
   removing the hub from the mold to provide a hub assembly comprising the hub and the strain relief;
   providing a catheter shaft having a proximal end; and
   subsequent to the step of removing the hub from the mold to provide a hub assembly, bonding the strain relief of the hub assembly to the proximal end of the shaft,
   wherein the step of injecting a polymeric material into the mold to form a hub includes the step of mechanically interlocking the strain relief to the hub.

2. The method in accordance with claim 1, wherein the strain relief includes a distal portion and a proximal portion, and wherein the step of inserting at least a portion of the strain relief into a mold includes inserting the proximal portion of the strain relief into the mold.

3. The method in accordance with claim 1, wherein a proximal portion includes one or more retaining grooves, and wherein the step of mechanically interlocking the strain relief to the hub includes mechanically interlocking the grooves to the hub.

4. The method in accordance with claim 1, wherein the step of bonding the strain relief to the shaft includes thermal bonding.

5. The method in accordance with claim 1, wherein the step of bonding the strain relief to the shaft includes adhesive bonding.

6. The method in accordance with claim 1, wherein the shaft includes a polymeric member disposed over at least a portion thereof, and wherein the step of bonding the strain relief to the shaft includes bonding the strain relief to the polymeric member.

* * * * *